United States Patent [19]
DiGiulio et al.

[11] Patent Number: 5,154,246
[45] Date of Patent: Oct. 13, 1992

[54] SENSOR PROCESSOR FOR HIGH-SPEED MAIL-HANDLING MACHINE

[75] Inventors: Peter C. DiGiulio, Fairfield, Conn.; Williams J. Linkowski, Poughquag, N.Y.; Francis E. McDermott, Watertown, Conn.; Edilberto I. Salazar, Brookfield, Conn.; Robert J. Tolmie, Jr., Brookfield, Conn.

[73] Assignee: Pitney Bowes Inc., Stamford, Conn.

[21] Appl. No.: 666,769

[22] Filed: Mar. 8, 1991

[51] Int. Cl.⁵ ............... G01G 19/40; G06F 15/20
[52] U.S. Cl. .............. 177/25.15; 364/464.03
[58] Field of Search ............ 177/25.15; 364/464.03

[56] References Cited

U.S. PATENT DOCUMENTS

| | | |
|---|---|---|
| 4,897,587 | 1/1990 | Digiulio et al. ............ 318/625 |
| 4,924,106 | 5/1990 | Tolmie, Jr. ............ 250/561 |
| 4,935,078 | 6/1990 | Bergman et al. ............ 156/64 |
| 4,956,782 | 9/1990 | Freeman et al. ............ 177/25.15 X |
| 4,959,600 | 9/1990 | Digiulio et al. ............ 318/625 |
| 5,007,054 | 4/1990 | Lee et al. ............ 371/32 |
| 5,044,452 | 9/1991 | Rand et al. ............ 177/2 |

Primary Examiner—George H. Miller, Jr.
Attorney, Agent, or Firm—Charles G. Parks, Jr.; Melvin J. Scolnick

[57] ABSTRACT

A sensor processor for cooperating with a drive controller in a high-speed mail-handling machine. The sensor processor access periodically a plurality of sensors distributed throughout the machine, and then writes the sensor data to an NVM-RAM shared with the drive controller. Time-critical sensors are accessed more frequently than non-time-critical sensors.

2 Claims, 6 Drawing Sheets

SENSOR PROCESSOR FOR HIGH-SPEED MAIL-HANDLING MACHINE

This invention relates to high-speed mail-handling machines, and in particular to a processor for responding to sensors in the machine for controlling various machine functions.

RELATED APPLICATIONS

U.S. application, Ser. No., 291,483, filed Dec. 28, 1988, entitled "HIGH-THROUGHPUT MAILING MACHINE TIMING";

U.S. application, Ser. No. 281,354, filed Dec. 8, 1988, entitled "MICROPROCESSOR MOTOR CONTROLLER HAVING DISCRETE PROCESSING CYCLES";

U.S. application, Ser. No. 291,473, filed Dec. 28, 1988, entitled "DRIVER CIRCUITRY FOR MULTIPLE SENSORS";

U.S. application, Ser. No. 291,092, filed Dec. 28, 1988, entitled "ENVELOPE FLAP PROCESSING APPARATUS".

BACKGROUND OF THE INVENTION

The above-noted, commonly-owned, related applications describe automatic mailing machines capable of handling mixed mail and capable of high-speed processing of mailpieces.

Automatic mailing machines typically include imprinting systems, such as a postage meter, where the information imprinted on the envelope or other sheet-like median is attributable to a variable parameter of the median, such as imprinting a postage value indicia on an envelope wherein the postage value is based on the weight of the envelope. In the mail processing field, it is desirable for a system operator to be able to deliver to mail processing equipment a batch of "mixed mail," that is, the batch is comprised of a large number of envelopes of varying dimensions, and variable thickness of weight. The ability of a mail processing system to process a large variety of mixed mail eliminates the need of the system operator from performing a preliminary step of presorting the mail. It is further desirable for mail processing equipment to be able to weigh the individual envelopes and affix the appropriate postage value indicia in accordance with the envelope weight. It is generally considered advantageous if the mail processing equipment can imprint a quality indicia upon envelopes varying in thickness from that of a postcard to approximately three-quarters ($\frac{3}{4}$) of an inch.

It is known to provide mail processing equipment comprised of a feeder for singularly delivering envelopes in series to a transport assembly. The transport assembly deposits the envelope on a scale for weighing. After a sufficient time to assure a true scale reading of the envelope weight, commonly referred to as "weigh on the pause", the transport assembly again assumes control over the envelope and delivers the envelope to a module commonly comprised of an integral transport assembly and attached flat bed postage meter. The mailing machine transport assembly assumes speed control over the envelope performing any necessary speed adjustments to the envelope required to match the envelope's traversing speed to the imprinting speed of the postage meter print drum to promote a quality indicia print. It is known for the postage meter to include a value setting mechanism and to adjust the postage meter printing mechanism for printing of the appropriate postage rate on the approaching envelope according to the envelope weight as determined by the scale. Reference is made to commonly-assigned U.S. Pat. No. 3,877,531 which describes in greater detail a prior art automatic mail handling machine.

It is desirable to provide a mail processing system as depicted above with (i) the capability to process a dimensionally wide variety of envelopes including thickness or weight, (ii) to do it as fast as possible in terms of envelopes per second, (iii) while applying a quality postage indicia.

The copending, commonly-owned application, Ser. No. 291,483, whose contents are incorporated herein by reference, describes a mailing machine for high-speed processing of mixed mail, capable of high throughput, and of compact size. It includes mail piece processing at four main stations or modules in a straight-through manner, under positive control at all times by separate drive units or transport means at each station, with the sequential processing actions timed to optimize mailpiece throughput. The controlling and timing is determined by signals received from a plurality of sensors distributed throughout the machine. In response to the sensor signals, a microprocessor issues drive and control signals to various operating mechanisms located at the mailpiece processing stations.

The copending commonly-owned application, Ser. No. 281,354, whose contents are incorporated herein by reference, describes a programmable microprocessor drive or motor controller and a programmable microprocessor sensor controller in communication with one another. The sensor controller is programmed to poll each of a plurality of sensors located at various places in the machine and store the sensor information until called for by the motor controller. The latter, in turn, in response to the sensor information outputs control signals along communication channels connected to a motor driver which actuates its assigned mechanism in accordance with the control information. Position servo-control and velocity servo-control, as is well known, can be incorporated in such a system. A sensor reading and motor control activating polling cycle is used, using a time-slicing cyclical approach, which is programmable, such that during each cycle, during its assigned time slice, each sensor is visited and its state read and stored. During other time slices of the cycle, motor control commands are issued. This system has the advantage that it manages time much more efficiently, which significantly contributes to the high-speed processing. Moreover, it is possible to program the microprocessors to schedule actions in different sequences for different machine modes, and to assign priorities to certain actions in order to increase the duration of the time intervals allocated to certain actions at the expense of other actions.

Despite the significant advances so far made for high speed processing of mail, these exists a continual need to improve the processing efficiency and increase the speed. A significant constraint is the limited time available to monitor the progress of a mailpiece through the machine. Individual monitoring is essential for mixed-mail processing since larger or thicker envelopes typically require different processing parameters than smaller or thinner envelopes. Moreover, in a complex machine wherein the envelope is subject to a large number of operations, e.g., singulation, thickness-measuring, flap-stripping, flap-sealing, weighing and indicia-printing, information concerning the status of the envelope at a previous station is essential for initiating actions at the next station. Hence, the machine controller must know within prescribed time intervals the status and condition of a number of machine events that are being carried out simultaneously or nearly simultaneously. As the mailpiece processing speed increases, the prescribed time intervals shrink.

A further constraint is economy. While real-time high speed monitoring might more readily be obtained with expensive, state-of-the-art computers, the costs thereof cannot be economically justified. Hence, a need exists to perform the functions above described with modestly priced controllers, typified by the 8051/8096 family. With this constraint, we have found that, to construct a sensor processing system following the teachings of the above-identified applications, creates certain problems which limits the processing speed attainable.

SUMMARY OF INVENTION

The present invention is directed to an improved sensor processor and an improved process for processing the sensor signals for generating outputs for communication to the drive or motor controller of a high-speed mail-handling machine.

According to one aspect of the invention, the present invention is based on the recognition that certain machine actions are critical and determinative of the machine's processing speed. In accordance with this aspect of the invention, the sensor processor is programmed to visit the sensors associated with those critical machine actions at least once during each main sensor cycle.

In a preferred embodiment in accordance with this aspect of the invention, the critical machine actions are locating the flap of the envelope on the fly so that it can be properly moistened before sealing, exiting of the envelope from the singulator, and deceleration of the envelope for proper registration with the indicia printer.

According to another aspect of the invention, a microcontroller is provided that is dedicated to the task of reading the sensors distributed throughout the machine and communicating the sensor data to the motor controller.

In accordance with a further aspect of the invention, the data communication is by way of shared memory. Preferably, the shared memory is non-volatile random-access memory (NVM-RAM).

SUMMARY OF DRAWINGS

Other features and advantage of the invention will be best understood from the detailed description that follows of a preferred embodiment of the invention, taken in conjunction with the accompanying drawings, wherein.

DETAILED DESCRIPTION OF PREFERRED EMBODIMENT

In order to understand operation of the sensor processor of the present invention, it would be helpful if a brief description of the machine were provided. This description is based on that given in the copending application, Ser. No. 291,483. While a preferred embodiment of the present invention will be described in connection with the machine described in the copending application, it will be understood that the invention is not limited in its application to that machine but can be applied to different mail-handling machines having different numbers of stations, different numbers of sensors, and operating with a different sequence of actions.

Figure 1:
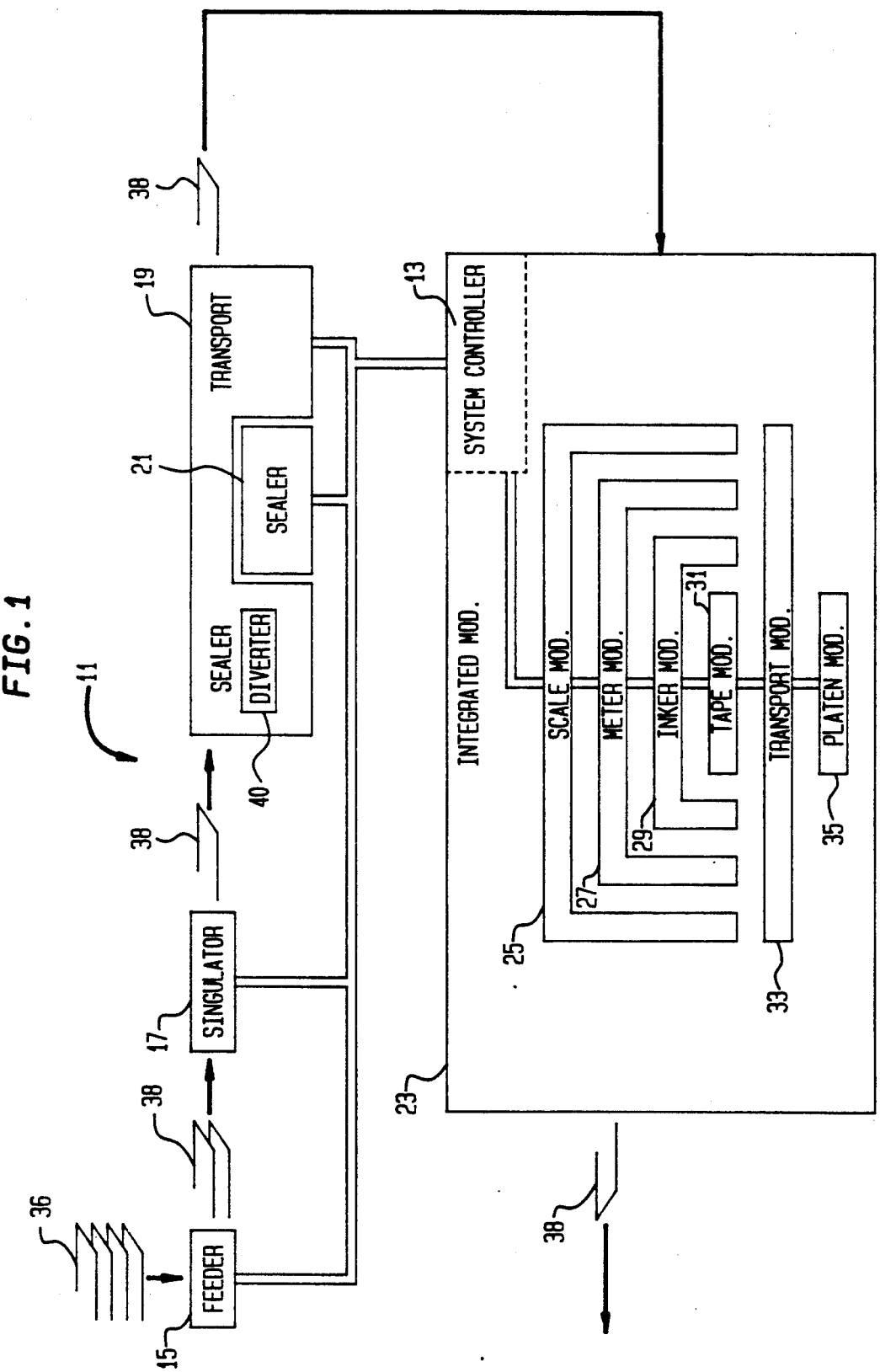
FIG. 1 is a schematic view of one form of mail-handling machine using the sensor processor in accordance with the invention.

Referring now to FIG. 1, a typical mail processing system employing the sensor processor according to the invention, generally indicated as 11, is comprised of a plurality of stations, preferably as modules, under the control and influence of a system controller, generally indicated as 13. The stations or individual modules are an envelope feeder module 15, a singulator module 17, a sealer module 19 which includes a sealer 21, and what is here referred to as an integrated module 23. The integrated module is comprised of a scale or weigher module 25, a meter module 27, an inker module 29, optionally a tape module 31, a transport module 33 and a platen module 35. The integrated module is so referred to because the individual modules are mounted in a single housing. Each module includes the appropriate mechanisms to perform a mail processing function.

Generally, the feeder module 15 receives an envelope stack 36 and, in the preferred embodiment, includes suitable mechanisms to shingle the bottom portion of the mail stack 36. The singulator 17 is charged with the function of extracting a bottommost envelope 38 from the now partially shingled envelope stack 36 in a seriatim manner and delivering the envelope 38 to the sealer transport module 19. The sealer transport 19 is charged with the function of traversing the envelope 38 across the sealer module 21. The sealer 19 has the capability of determining the sealing state of the envelope 38, and includes a diverter arm 40 for stripping open closed but unsealed envelope flaps, for responding to the seal state of an envelope such that only unsealed envelopes 38 are subject to sealing by the sealer module 21, and for detecting mis-sealed envelopes. The sealer transport serves up the envelope 38 to the transport module 33 of the integrated module 23.

The mailing machine transport module 33 receives the envelope 38 from the feeder transport 19 and delivers the envelope to the scale 25. The scale module 25 is charged with the function of weighing the envelope 38 and reporting the appropriate postage value as a function of its weight to the postage meter module 27 mounted to the mailing machine 23. The indicia printing method employed in the preferred mailing system is referred to in the art as flat bed indicia printing. In accordance therewith, as the envelope 38 rests upon the scale, subsequent to being weighed, the postage meter module 27 print elements are set to the appropriate value as a function of envelope 38 weight. The inker module 29 is then charged with the function of inking the indicia of the meter module 27. Subsequent to inking of the postage meter module print elements, the platen module 35 is charged with the function of bringing the envelope 38 into printing contact with the print elements of the postage meter module 27. After the envelope 38 has been imprinted by the postage meter module 27, the transport module 33 resumes control over the envelope 38 and ejects the envelope 38 from the mailing machine 23.

Figure 2:
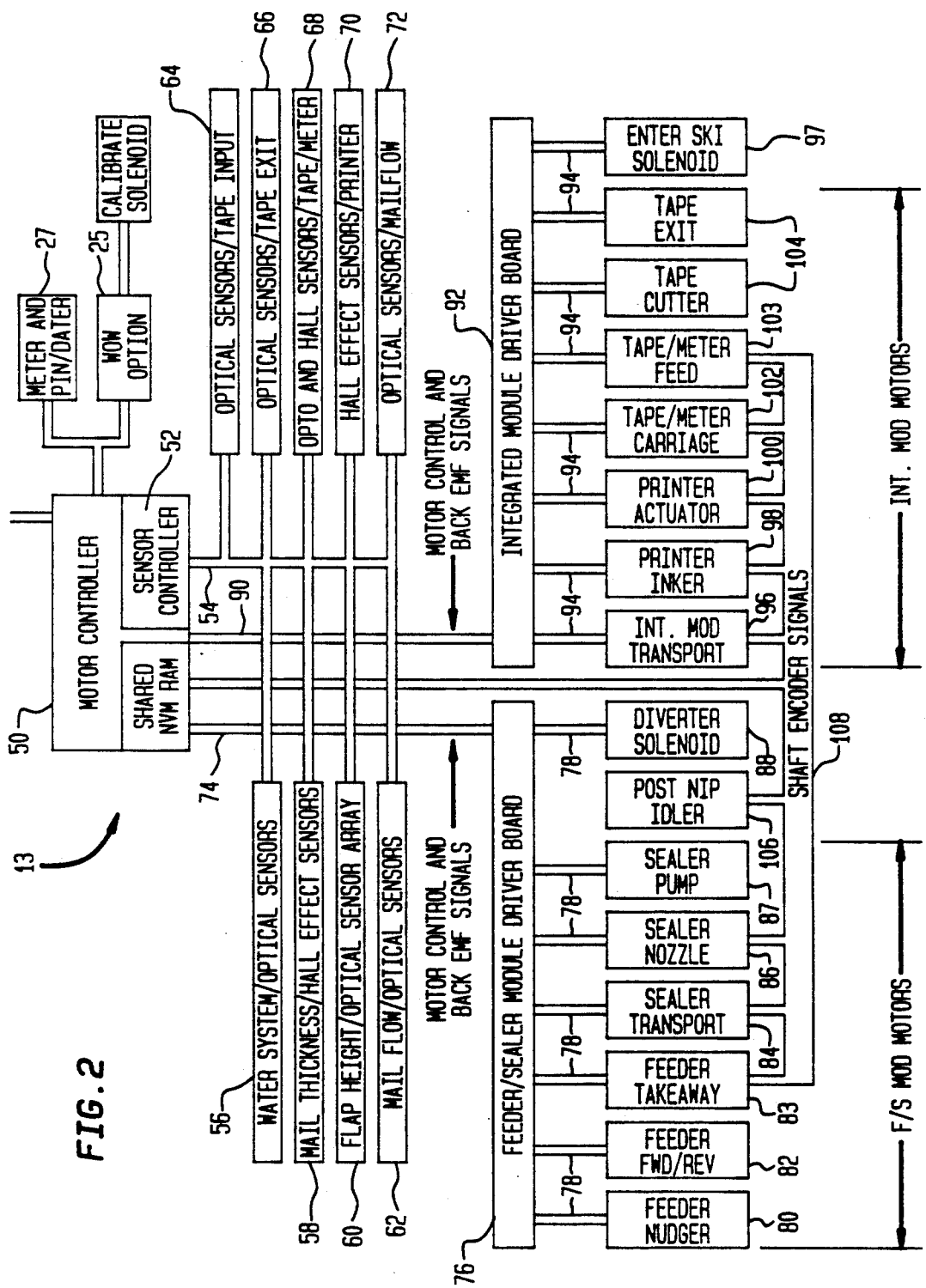
FIG. 2 is a system schematic illustrating how the various mail processing functions for the machine of FIG. 1 are activated and monitored.

Referring to FIG. 2, the controller system, generally indicated as 13, includes a programmable microprocessor motor controller 50 and a programmable microprocessor sensor controller 52. A host processor (not shown) provides overall supervision of the motor controller and sensor controller and interfaces to the machine operator. The motor controller 50 and sensor controller 52 are in direct parallel communication. Preferably, this communication occurs by way of shared memory, in particular non-volatile random-access memory (NVM-RAM). In general, as will be explained in greater detail below, the sensor processor reads substantially all sensor data, processes as necessary, and stores or writes same in the NVM-RAM at specified locations. The motor controller, in turn, can read and write to the same or different memory locations, and thus can use the current status of the sensors, as established by the sensor controller, to provide command information for the drives and motors operating the various modules. Generally, the sensor controller 52 is programmed to poll each of a plurality of sensors located at various places in the machine and store the sensor information until called for by the motor controller 52.

A sensor bus 54 communicates the sensor controller 52 with a plurality of sensors and sensor banks, shown only schematically. For example, the sensor controller 52 is in bus 54 communication with a plurality of sensors and sensor banks associated with the various modules 15, 17, 19 and 23, such as: optical sensors 56 associated with a water system for the sealer module 21; Hall-effect sensors 58 associated with the singulator module 17 for determining the thickness of an envelope 38; an optical sensor array 60 for determining the flap configuration of an unsealed envelope 38 associated with the sealer module 21; mail flow optical sensors 62 associated with the respective feeder section modules 15, 17 and 19 for sensing the time position of the envelopes 38 relative to the respective feeder section modules 15, 17 and 19; optical sensors 64 associated with the tape input to the tape module 31 and optical sensors 66 associated with the tape exit from the tape module 31; optical and Hall-effect sensors 68 associated with the tape module 31 motor drive system and meter module 27 loading drive system; Hall-effect sensors 70 associated with the platen module 35 drive system; and optical sensors 72 associated with the integrated module 35 for sensing the time-position of the envelope 38 within the integrated module 23.

It should be understood that suitable module assemblies acting under the motor influences is a matter of design choice. It should be further understood that the motor controller systems 13 will function cooperatively with any suitable mechanism system. The mechanism system here generally described is used for the purpose of illustration and sets forth one preferred environment for the subject invention.

The motor controller 50 communicates through a first bus 74 with a first motor driver board 76. The driver board 76 may be located within the integrated module 23. Alternatively, the feeder section modules 15, 17 and 19 may also be mounted in a single housing also housing the driver board 76. The driver board 76 in turn is in respective bus 78 communication with a plurality of motors associated with a respective feeder section modules 15, 17 and 19, such as, motor 80 associated with the feeder module 15, motors 82 and 83 associated with the singulator module 17, motor 84 associated with the sealer transport module 19, motors 86 and 87 associated with the sealer module 21, and a solenoid motor 88 which may be optionally associated with the diverter 40.

The motor controller 50 also communicates through a second bus 90 with a second motor driver board 92. The driver board 92, in turn, is in respective bus 94 communication with a plurality of motors associated with the modules 25, 27, 29, 31, 33 and 35 of the integrated module 23. For example, the driver board 92 through bus 94 communicates with motors 96 and 97 associated with the transport module 33, a motor 98 associated with the inker module 29, a motor 100 associated with the platen module 35, motors 102 and 103 associated with the tape/meter modules 29 and 31, and motor 104 associated With the tape module 29. It should be noted that a single driver board may be employed.

A plurality of the motors may include encoding apparatus enabling the respective motors to be under position servo-control of the motor controller 50, for example, motors 83, 84, 86, 96, 98, 100, 102, 103 and 106. An idler encoder mechanism 106 here associated With the singulator or the sealer transport module 19 is included to provide true speed data for a traversing envelope 38 to the motor controller 50. The respective motor encoders are in bus 108 communication with the motor controller 50. The motor controller 50 can also communicate with ancillary and/or auxiliary system, such as, the meter module 27 and the scale module 25. The motor driver boards 76 and 96 are preferably comprised# of a plurality of channels. Each channel is associated with a respective motor and includes a conventional H-bridge amplifier responsive to a pulse width modulated signal generated by the motor controller 50. Any of the desired motors may be subject to position servo-control and/or velocity servo-control as is well known, the respective motor driver boards 76 or 92 channel further including a conventional EMF (Electro Motive Force) circuit for deriving the back EMF of the respective motor and communicating the back EMF to the motor controller 50 through the respective bus 94 or 90 or from which velocity information is obtained.

The details of the motor controller 50 software interfaces with the various operational units is not important to this invention, and for further information, reference is made to said copending application.

Generally speaking, the motor control system 13 is responsible for the activation and control of all motors and assemblies associated with the system modules. While mail processing includes the control of transport motors in the feeder, singulator, sealer, and integrated modules, mail processing may also include operator selectable functions. For example, in accordance with the mail processing system 11, the operation options are set forth in Table 1.

TABLE 1

| MAIL PROCESSING OPERATING MODE MATRIX | | | |
|---|---|---|---|
| | PRINTING | SEALING | WEIGHING |
| FLOW ONLY | OFF | OFF | OFF |

TABLE 1-continued

| MAIL PROCESSING OPERATING MODE MATRIX | | | |
| --- | --- | --- | --- |
| | PRINTING | SEALING | WEIGHING |
| WEIGHT ONLY | OFF | OFF | ON |
| SEAL ONLY | OFF | ON | OFF |
| NO PRINT | OFF | ON | ON |
| PRINT ONLY | ON | OFF | OFF |
| NO SEAL | ON | OFF | ON |
| NO WEIGHT | ON | ON | OFF |
| FULL FUNCTION | ON | ON | ON |

The sensor controller of the invention will only be described in connection with the full function mode described in Table 1, referred to hereinafter as the "mail flow" mode, and a diagnostics mode not illustrated in Table 1. The invention be fully understand in its application with respect to the mail flow mode, because the latter includes essentially all of the time-critical functions. Modification of the sensor processor to handle the other modes is relatively simple and will be evident to those skilled in this art. The details on the operation of the motor controller, provided with the sensor information via the shared RAM, are not important to this invention and have been omitted, but these details can be found in the referenced copending application.

A generalized description of the manner in which the machine processes mail, and some of the factors involved in its design, constraints and performance will now be given to make clearer the description of the sensor processor modules that will follow hereinafter.

Figure 3:
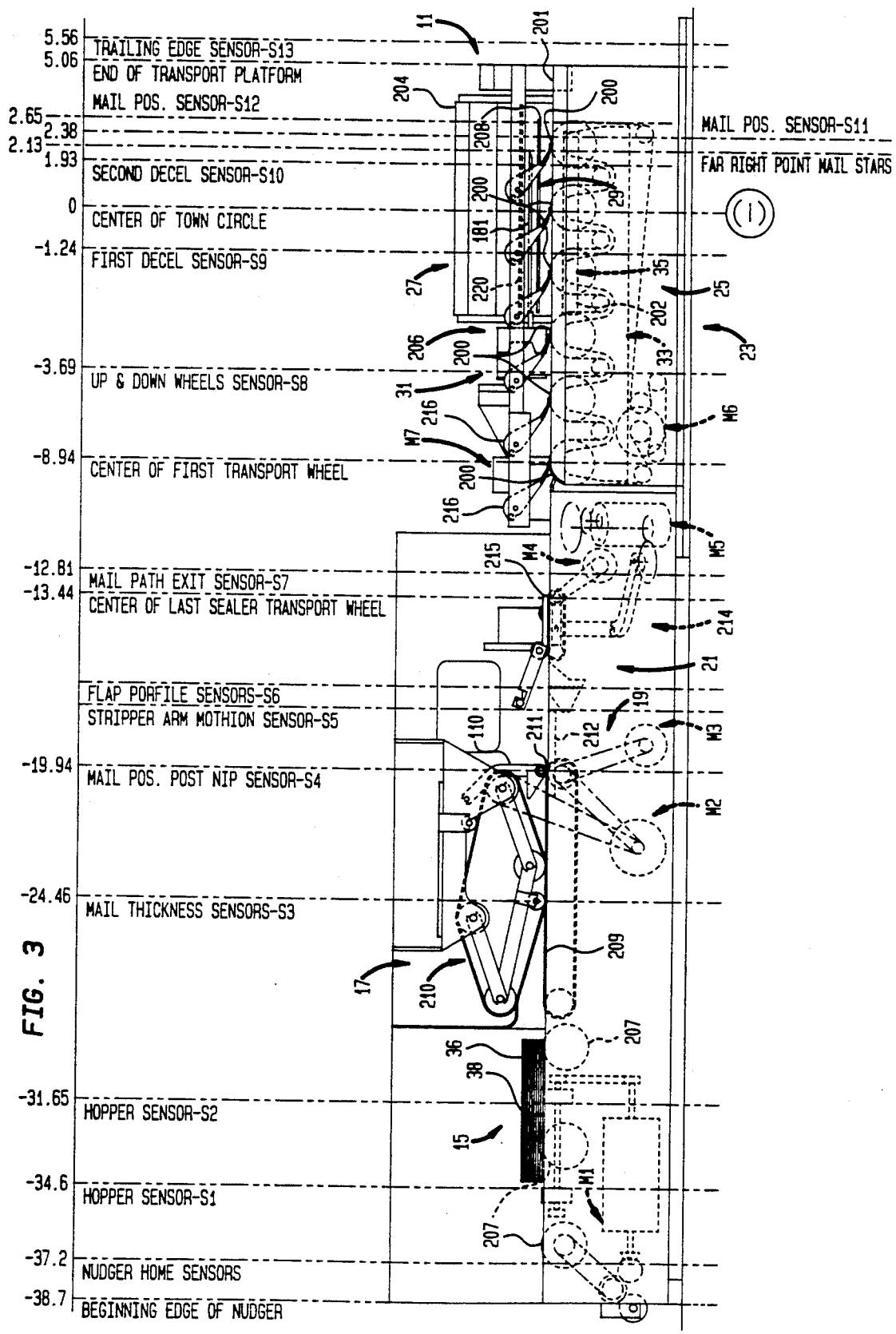
FIG. 3 is a side view of the mail handling machine of FIG. 1 wherein components involved in the machine's timing are indicated.
Figure 4:
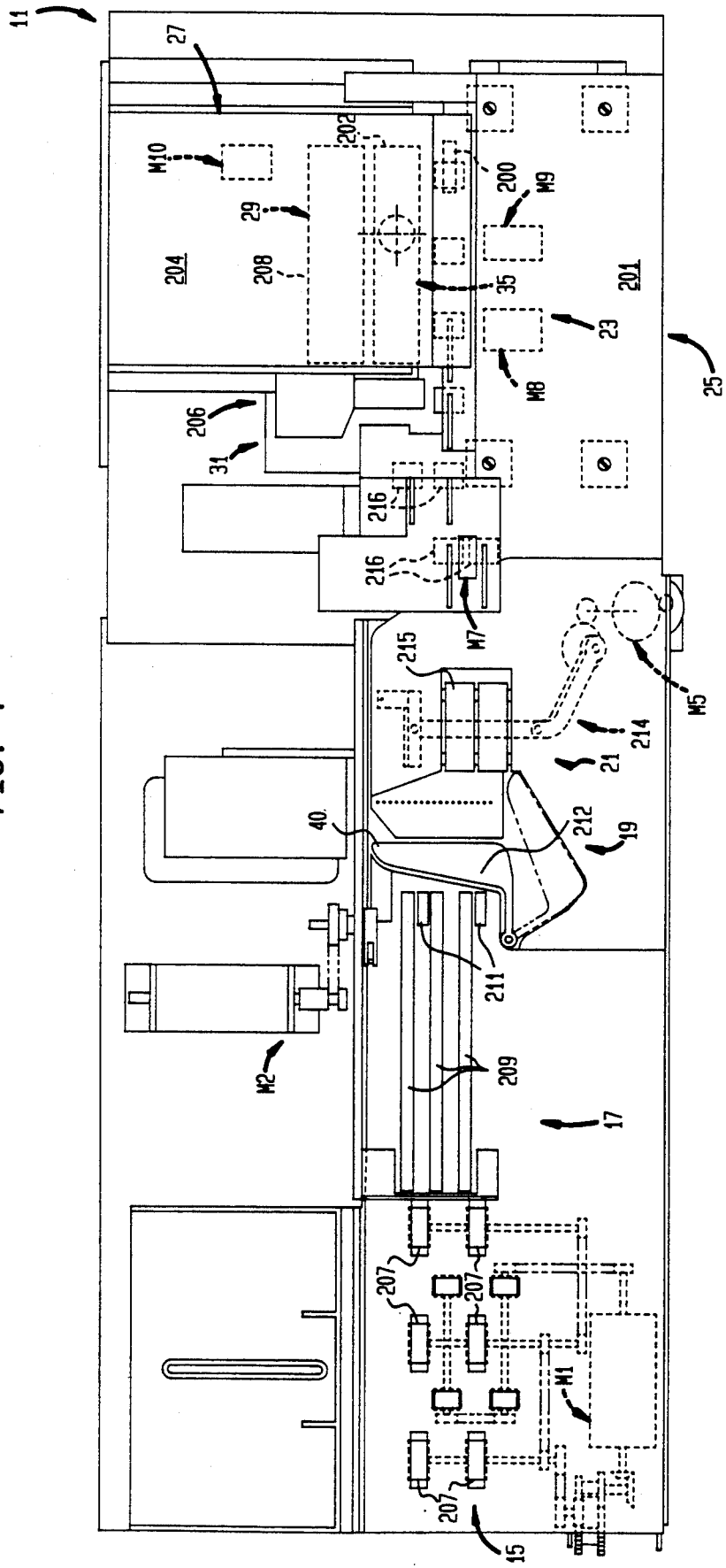
FIG. 4 is a top view of the machine depicted in FIG. 3.

Referring to FIGS. 3 and 4, inside the integrated module 23 is a transport assembly comprised of a plurality of rollers 200 independently supported by the mailing machine base in a manner which permits the rollers 200 to assume a vertically engaged position (up position) for contacting an envelope on the deck 201 above for transporting same, or a vertically disengaged position (down position) out of communication with the envelope. Each roller is aligned to journey through a respective slot in the deck. A bidirectional drive motor assembly M6 is in communication with each roller via an endless belt. The drive motor assembly includes a one way clutch interactive with the transport assembly such that motor actuation in one direction results in the endless belt imparting a forward driving force to each roller, and motor actuation in the opposite direction causes the transport assembly to reposition the rollers in its down position.

The sealing assembly is mounted in the mailing machine in a suspended manner over a leading portion of the weighing plate of the scale and includes a plurality of sealing members selectively positionable in a first position, biased downwardly to seal wetted envelope flaps, and in a second position in an upwardly retracted position for pre-sealed envelopes.

The mailing machine further includes a vertically displaceable platen assembly 202 mounted to the base of the mailing machine and aligned for cooperatively acting with a suitable postage meter 204 mounted above.

The tape module 206, if present, provides a tape track in a generally cantilevered manner to extend generally below and to one side of the meter module. The tape module can be selectively positioned in a first position such that the tape track is located longitudinally below and vertically between the printing means of the meter module and the platen assembly. In a second position of the tape module, the tape track is positioned longitudinally below and longitudinally in spaced relationship to the printing means of the meter module and the platen module. The tape module includes a tape feed which can selectively deliver to the tape track one of two types of tape for imprinting by the meter module.

The mailing machine further includes an inking mechanism for depositing ink on the meter print elements, which include an inking pad 206 which is moved into contact with the print elements.

At the upstream end of the machine, feeder rollers 207 activated by drive M1 carries the envelope into the singulator section 17, where they are forward driven by forward belts 209 controlled by drive M2 while a trapezoidal four-bar linkage 210 above is reversely driven to drive back all but the bottommost envelope. The envelope is then stopped under the linkage 210, its thickness measured by sensors there, and the envelope awaits activation of the take-out or post nip 211 for passing the envelope to the sealer section 21, where a stripper arm 212 strips open the flaps of unsealed envelopes and detects mis-sealed envelopes. The envelope flap profile is then recorded and used to control a moistener 214 downstream via spray from a motor-activated nozzle, and the envelope enters the sealer nip 215, just before entering the integrated module 23. In the integrated module, two so-called skis 216 can be selectively engaged or disengaged to the envelope top to apply vertical pressure. When engaged, the envelopes are driven forward; when disengaged, even if the transport wheels 200 are moving forward, the envelope remains stationary. The transport system properly positions the envelope on the weighing plate of the scale underneath the meter module 27. The transport rollers 200 are then caused to withdraw by reversely driving the motor M6 for the transport rollers. Simultaneously, the inking module 29 has been actuated to apply imprinting ink to the registration area of the postage meter module 27 and then withdrawn prior to the arrival of the envelope. Upon the arrival of the envelope in proper position at the weighing station and withdrawal of the transport rollers 200, the scale module weighs the envelope, in a manner described in U.S. Pat. No. 4,778,018, and informs the meter for meter setting, in a manner described in pending application, Ser. No. 114,358, filed Oct. 27, 1987, entitled PRINTWHEEL SETTING DEVICE FOR A POSTAGE METER. Subsequent to weighing of the envelope, the platen module 21 is actuated, in the manner as afore-described, to result in the imprinting of an indicia on the envelope. Simultaneously with actuation of the platen module 21 or pursuant to a minimum time lag, as will be later described, the transport rollers 200 can be reactivated or further activated to return the rollers 200 to their first position. Upon obtainment of the first position of the rollers, the envelope is discharged from the mailing machine. Simultaneously with commencement of discharge of the process station envelope from the process station, a new envelope may be received by the transport module 12.

Further, the optional capability is provided for imprinting an indicia on one of a plurality of tape median. The tape module 17 can be positioned for imprint of a indicia on one of two tapes carried by the tape module 17. The vertical elevation of the tape track is below the vertical position of the ink pad well such that the tape track 181 does not interfere with the operation of the inking module 17.

The meter print wheels, for security reasons, when not printing, are covered by retractors 220, sometimes referred to as shutters or rectifiers, which are moved out of position to expose the print wheels just before inking by the ink pad.

A more detailed description of the operation is given in conjunction with the various sensors indicated by the vertical dash-dot lines in FIG. 3. The numbers at the top of the vertical lines represents the spacing of that line from a zero position known as the center of town position. Upstream spacings are negative; downstream spacings positive. The center of town position corresponds to the location of standard indicia imprinted on envelopes by postage meters. The relative dimensioning of the machine will be appreciated from the size of a standard No. 10 envelope, oriented horizontally or flat, with its short side leading, indicated at 38.

There are a number of sensors located at various positions within the machine, and those involved in the machine's timing are shown in FIG. 3. The others, which include, for example, sensors indicating home positions for an envelope flap tamper, the nudger, the water pump, the platen-actuator, the inker, are not shown, nor are shown such sensors as those for indicating water level, water spray and various meter security measures.

Referring now to those figures, two sensors S1 and S2 are located as shown in the hopper region for the first feeder section 15. The two sensors S1, S2 cover the hopper region and signal the controller that more envelopes need processing. The feeder forward drive 207 is controlled by motor M1. This drive when activated advances the envelopes in shingled fashion downstream toward the singulator section 17, while simultaneously nudging the envelopes against a rear registration wall.

The forward drive 209 for the singulator section is driven by motor M2 which is coupled to the four bar linkage 210 that is reverse driven to effect envelope singulation. The thickness measuring sensor S3 is connected to the four bar linkage. The take-away or post nip 211 in the singulator section is driven by motor drive M3 or alternatively by the singulator drive M2. At approximately the same position is located a mail position sensor S4 for determining whether a mail piece is present at the post nip.

The forward drive for the next sealing section 21 is designated 215, driven by motor M4 and is referenced as the sealer nip. As described in copending application, Ser. No. 291,099, a flap stripper blade 212 in the sealer is connected to a sensor S5 which indicates when the blade is moved. In the same section is located the unsealed-flap moistener 214, actuated by a motor drive M5. The latter is controlled by the flap profile generated by a profile sensor S6. The exit sensor for a mail piece from the sealer section is designated S7.

The forward drive in the integrated module 23 is designated M6. A number of sensors are associated with this module. A sensor S8 indicates whether the forward drive wheels 200 are up, which means that a mail piece present may be advanced, or down indicating that no advancement movement occurs. The action works with the two leading transport skis 216, which also can be positioned up, for no forward movement, or down for forward movement, actuated by motor M7. In addition, two spaced decelerate sensors (abbreviated decel) S9 and S10 are present, one at each side of the town circle center, which locates the position the envelope should occupy for proper printing. The location indicated by the label "Far Right Point Mail Stars" is the furthest downstream point of the printed indicia. The envelope must be positioned at least 0.5 inches downstream from this point for proper printing. Two mail position sensors S11 and S12 are located downstream of that point. The last sensor S13 detects the trailing edge of the imprinted envelope ejected from the machine.

Shown schematically are a motor drive M8 for the inker. In the preferred embodiment, the inker applies ink to the printer indicia just before each printing to the envelope. Printing takes place by raising the platen 202 supporting the weighed envelope by motor drive M9 and pressing it against the printer wheels, previously set by the weight information obtained from the scale. The meter is kept normally locked for security purposes by a set of retractors activated by motor drive M10. When an envelope is ready to be imprinted, the retractors are activated and withdrawn so printing can occur. After the printing, the retractors are activated to relock the printer.

In the preferred mode of operation, the operator places, say, two envelopes into the hopper section at the left end of the feeder 15. This trips the hopper sensors S1, S2 and the status is sent to the controller of the system. Once started the transport 207 then moves the mail pieces into the singulator forward and reverse drive area. At this time, the mail is being singulated by the reverse drive belt 210 (during singulation the mail piece will lift up the four bar linkage mechanism which has an array of sensors S3 on it which will be used in determining the mail's thickness) and the forward drive belt 209 carries the first mail piece through the feeder until it trips the mail position post nip sensor S4. Once the sensor S4 has been tripped the feeder M2 is then decelerated to stop the first mail piece's lead edge one-half inch downstream of the sensor S4. Once stopped, this is considered the mail piece's feeder wait position. This is when the mail piece's thickness is measured, and at that point the thickness, along with a velocity profile, is sent to the controller.

At this time the feeder including the drive M3 for the take-out nip is awaiting a start command to be sent from the controller. Once the command is received, the feeder then carries the first mail piece into the sealer transport area and the second mail piece is fed into the four bar linkage area of the singulator and comes to rest in the feeder wait position.

The first mail piece is picked up by the first wheel of the sealer transport 215 and is carried through the sealer. As described in the copending application, Ser. No. 291,099, if the detector arm 212 is moved by the advancing envelope, then a number of actions take place to determine whether the envelope may be missealed and processing should stop to avoid jamming the machine. This is described in detail in the copending application and need not be repeated. Assuming the mail piece is satisfactorily sealed, once the first mail piece's trailing edge trips the mail path exit sensor S7 (which is located $\frac{3}{8}''$ downstream from the center of the last sealer transport wheel) then the sealer is decelerated and then stopped. At this time the first mail piece is already 5" into the integrated module transport 23. When the leading edge of the first mail piece is 7.7" into the integrated modules transport, it then trips the first decel sensor S9 and the transport M6 starts rapidly decelerating. Prior to the first mail piece being seen by the second decel sensor S10, the meter retractors 220 are retracted and the feeder M2, M3 starts up to send the second mail piece into the system. When the first mail piece is 3.17" downstream from the first decel sensor S9, it then trips the second decel sensor S10 and the transport M6 is gently decelerated to a stop. Just prior to the first mail piece coming to a stop, the inker completes its inking cycle. At this time the mail position diagnostic sensors are checked to see if the first mail piece has tripped either the first S11 or both the first S11 and second S12 position sensors. If the first mail piece is not seen by the first mail position sensor S11 (this is termed improper registration), then the transport is turned on to move up the first piece to trip that sensor. If the first sensor or both the first and second sensor have been tripped, then the platen-actuator M9 is allowed to continue its travel to print the indicia.

When the platen-actuator 202 starts returning to its home position, this notifies the controller that the print cycle is complete, and the meter 15 is sent a command to extend its retractors 220. When the platen-actuator 202 has dropped below the ink tray level, the transport M6 has reached its peak velocity to carry the first mail piece out of the system. While the first mail piece is being carried out of the system, the second mail piece has already entered the integrated modules transport, but its trailing edge has not been detected by the sealer's mail path exit sensor S7 to turn off the sealer transport. By the time the second mail piece has reached the mail position sensors S11, S12, the first mailpiece has already exited the system.

The process is the same for the second mailpiece until it exits from the system. After the second mailpiece left the hopper area of the feeder, the hopper status of empty was sent to the controller. So when the second mailpiece is exiting the system the trailing edge sensor S13 (which is located one half inch downstream from the end of the integrated module platform) is monitored. Once the sensor has seen the trailing edge of the second mailpiece (which is also the last mailpiece in the system) then the transport sends a message that mail processing is complete and the controller sends back a command to shut down the system.

Several of the features of the invention involve dedicating a microcontroller to the task of determining sensor status and communicating such information to other entities that require it. In the machine described in the introduction, the other entities include the motor controller which requires certain of the sensor data to control the mail stations, and also a host processor. The host acts to provide a suitable interface with the user and also to perform certain high level activities including postage value accounting. In its role in the user interface, it controls a display which communicates operating information to the user, such as the existence of a jam, the jam location, the water level in the sealer and tape modules, and various meter security information. The host therefore also needs access to certain of the sensor data. There are various ways in which one microprocessor can communicate with one or more other microprocessors, but we have found that shared RAM offers by far the fastest way possible, as well as the easiest way for multiple microprocessors to communicate. While conventional computer science techniques have to be incorporated to prevent contention arising among the microprocessors, as a result, for example, of simultaneous attempts to access the RAM by two or more microprocessors, it turns out that the protection mechanisms needed, such as synchronization and the use of semaphores to prevent contention, consumes little CPU time. It should be noted that, in the preferred mail-handling machine, all three processors must have the capability to read and write to the same shared memory, though two microprocessor will rarely write and read to the same memory locations. In the protection scheme employed, the memory access requests are prioritized, with the motor controller having the highest priority, the sensor controller the next highest, and the host the lowest priority.

Especially in the environment of a mail-handling machine which involves postage value, it is important that the communication of data among the microprocessors be reliable. Shared RAM does not have the benefits of such data checking schemes as parity and CRC checks used in other data communication means. But we have found that, in accordance with a further feature of this invention, the reliability can be raised to a sufficiently high level to satisfy commercial concerns by employing non-volatile RAM (NVM-RAM). NVM-RAM offers an additional level of protection against accidental loss or corruption of the stored sensor data.

In accordance with another feature of the invention, many of the sensors directly generate analog data, and the sensor processor is configured to convert that analog data into digital data and store in the shared RAM the digital sensor data.

The machine so far described in detail to provide the environment of the present invention, as previously noted, is just one possible configuration out of many. A feature of the invention is that the sensor processor is very versatile and easily adapted to different machine configurations, or different arrangements of sensors, or different numbers of sensors. The common attributes will be a multi-function mail-handling machine designed for high speed mail processing and provided with a plurality of sensors distributed throughout the machine and detecting a physical parameter of the mailpiece, such as size and weight, or the position or velocity in the machine of the mailpiece, or a physical parameter of a machine module. The latter, for example, could include in the sealer, the water level; in the meter, the position of its shutter (which protects the print indicia) or its security; in a tape unit, the water level and temperature, or the position of a cutter. The important consideration is that in every such machine, the status of certain sensors will be time-critical, and others will not be. In other words, the sensor functions can be divided up into several categories, with a first category holding the time-critical sensors, and at least one second category holding non-time-critical sensors. Depending upon the time constraints imposed, the sensors in the second category can be divided up among second and third, or more categories, with the read-sensor cycle time being the categorization basis. This will be clearer with reference to the machine so far described.

Suppose that the main sensor cycle has been chosen to be 1 millisecond (ms), and that the desired mailpiece throughput is 4/s. That means, in general and in rough numbers, each mailpiece is allocated 250 ms to enter the machine, be processed, and be ejected. Thus, in the time it takes one mailpiece to traverse the machine, the sensor controller can execute 250 read-sensor cycles. In the machine so far described, there are four events that fall into the time-critical category. The first is reading of the post nip sensor, which indicates the time when a mailpiece starts its individual journey through the machine, or, equivalently, the gap difference between successive mail pieces. The upstream processing is to provide a single mailpiece, registered against a registration surface, ready to be processed. It waits at the post nip position until the previous envelope has cleared or is being cleared from the machine, and then is accelerated into the sealer. Since certain downstream actions begin at post nip time, or shortly thereafter, this point in time must be accurately determined. Hence, the post nip sensor is read twice each ms.

In the integrated module, the envelope must be oriented relative to the fixed print indicia. It enters the integrated module at high speed and therefore must be decelerated in a controlled manner so that it will come to a full stop in the proper position. Two deceleration sensors are provided, which detect in sequence the leading edge of the mailpiece and control the motor drives which bring the envelope to a stop. Hence, one each of these two sensors must be read once each ms.

The third time-critical event is the writing and reading of the shared NVM-RAM. Sufficient time must be allocated during the sensor cycle for the sensor controller to communicate with the shared RAM.

The sealer station also employs a sophisticated flap sealer which scans the flap of the envelope, on the fly, calculates the gummed area, and then directs a spray nozzle to spray water on the gummed area as the envelope flies by overhead. A number of sensors are read during this operation. This is time critical and represents the fourth time-critical event that will be read twice each ms.

There are other machine events that fall into a second category which is not as time critical as the first. For instance, the sealer station has a sealer exit sensor, indicating when the mail pieces leaves the sealer, and a sealer flow sensor, indicating the mailpiece position within the sealer. The status of these sensors is important because certain actions are started in the integrated module when the sealer flow and sealer exit sensors are tripped. However, for this particular machine, there is a tolerance of tens of milliseconds within which the tripped time of these sensors need be known. Hence, they need not be read once each cycle, and can be read less often. In the examples given below, each of these sensors are read alternately during the same time slice.

The sealer described is provided with a mis-sealed flap detector, comprising an arm connected to a Hall-effect detector, which is activated when the arm encounters a mis-sealed flap. The response of the machine is to slow the drives to determine whether the mailpiece will pass through the sealer. If not, it represents a jam and the machine is stopped to allow an operator to remove the stuck mailpiece. This is therefore deemed a second category event, and the Hall-effect sensor is read at one-half the frequency of the flap and post-nip sensors.

The remaining sensors fall into the third category of clearly non-time-critical or slow sensors. For example, a slow sensor reads the water level in the sealer. Since about 250 main sensor cycles occur per envelope traversal time, the water level can change very little, if at all, during these 250 sensor cycles, and thus such a sensor need only be read once per tens or hundreds of the main cycles. Into this same slow category fall water temperature sensors, mail in hopper sensors, meter security and key switch sensors. This category of slow sensors is treated by allocating one time slice during each cycle for reading one of the slow sensors. Hence, if, for example, 25 slow sensors are present, then each of the 25 would be read in turn during successive cycles, thus requiring 25 cycles or 25 ms to read all of the slow sensors.

Other variations are obviously possible. For example, a cycle counter can be provided and some slow sensors read only after the counter has reached a predetermined value. With a faster processor, several slow sensors can be read during each main cycle.

The versatility of the system is evident from the foregoing example. It is very easy to add additional slow sensors to the system, since even if the number were doubled—say 50 instead of 25—it still would consume only 50 ms to read each of the slow sensors. Moreover, it would take only little revision of the software to add additional or subtract modules to or from the machine. If an additional module has a second category sensor, then it could be read during the time slice allocated for the sealer flow and exit sensors. Additional or fewer slow sensors are easily added or deleted from the system.

Figure 5:
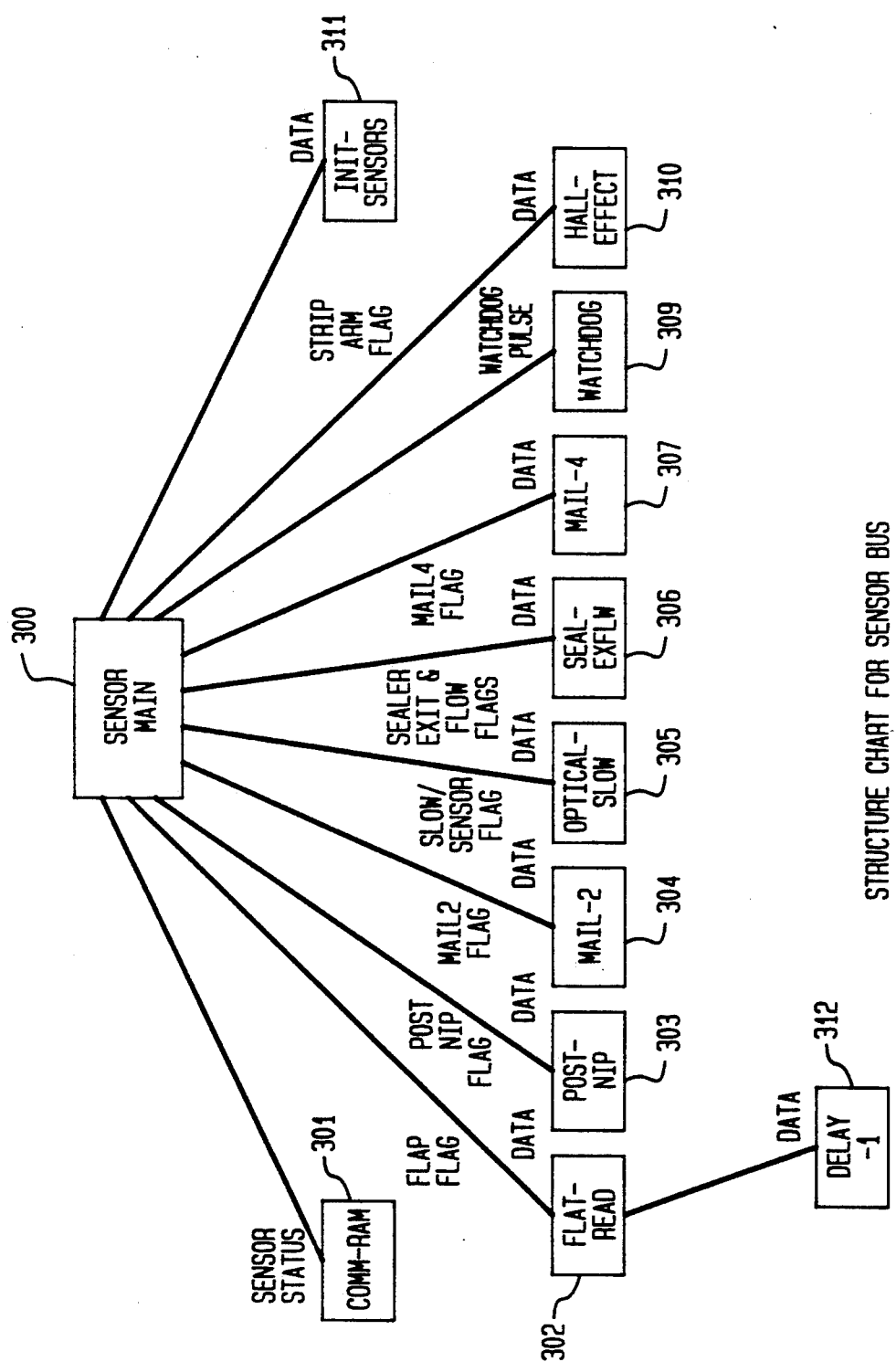
FIG. 5 is a structure chart of the software modules used in one embodiment of the sensors processor of the invention, for a machine of the type illustrated in FIGS. 3 and 4.

There now follows a detailed description of the software for one sensor processor that has been created for a machine similar to that described above. However, some of the sensor names used are different from those previously described, some perform additional functions, and some present in the described machine have been omitted. These differences are not important to an understanding of the invention. The description that follows can be best understood with reference to FIG. 5, which is a structure chart of the software and also includes data transfer and other status information. The concept that will be evident from FIG. 5 is that there exists a main program 300 which will call in sequence ten modules in the mailflow mode with no interrupts and one extra module in the diagnostic mode with interrupts. Before describing in detail the software modules, it is important to understand certain of the terms used to describe their functioning. These terms also involve other aspects of the invention.

In accordance with a feature of the invention, incorporated in the system is means to assist in diagnosing malfunctions in the machine. In view of its high speed processing, it is very difficult with the naked eye to observe the exact sequence of actions that takes place when a mailpiece is processed. Thus, we have found it useful to employ a high-speed camera with strobe illumination with the camera shutter and strobe triggered at certain prescribed regular intervals, obtained by generating a strobe pulse at those regular intervals. However, this can sometimes corrupt other sensor outputs if the camera strobe happens to occur at the same time as a sensor output. This is overcome in the following manner.

When the machine is placed in a diagnostic mode, an interrupt is generated in a periodic manner within the sensor controller. This is the only time that the interrupt mechanism of the sensor controller is used. A typical interrupt cycle would be once each millisecond. When the diagnostic interrupt is generated, the sensor controller executes a routine which generates the camera strobe pulse and sets a flag called the Camera Strobe flag. The sensor controller is also polling the sensors as indicated above both before and after each diagnostic interrupt. When in the diagnostic mode, the controller checks the Camera Strobe flag after each sensor or plurality of sensor readings for that event has occurred, that is, after each module routine is executed.

If the Camera Strobe flag is set, indicating that a camera strobe had been generated which may have occurred while the sensors were read, then the sensor controller clears the Camera Strobe flag and rereads the same sensors previously read by re-executing the same module. If the Camera Strobe flag was not set, then the sensor controller writes the sensor outputs to the RAM, and executes the next sequential module. Since the Camera Strobes occur approximately once each polling cycle, only occasionally would it interfere with one of the sensor readings. This feature is only used during diagnosis of a machine malfunction, where it may be necessary to hook up a high-speed camera to assist in the diagnosis. The circuitry and software to achieve the foregoing have not been illustrated, except in the dataflow diagram of FIG. 5, as their implementation would be evident to anyone skilled in the art. The label FLAG or FLAGS employed in the FIG. 5 diagram represents the Camera Strobe flag described above, which is checked during the diagnostic mode after execution of the indicated modules, as well as other flags described below. In the operational modes, the check Camera Strobe flag routine is not executed.

Included in each polling cycle is a module known as the Watchdog 309. The Watchdog module functions to prevent overheating of the optical sensors. In the preferred embodiment of the invention, the optical sensor system described in copending U.S. application, Ser. No. 291,473, is employed, whose contents are hereby incorporated by reference. In that system, each optical sensor comprises an LED and a photodetector. Each LED and photodetector has two leads, one of which is to be connected to a current source, and the other of which is to be connected to a sink. The LED is activated when its source and sink leads are connected, respectively, via suitable circuits to, for example, +5 volts and ground, and the photodetector will conduct current in its sink lead when its source and sink leads are similarly activated. The combination LED-detector units are electrically arranged in a matrix in which each row of the matrix corresponds to a bank of the units, and each column of the matrix corresponds to units whose LED and detector source leads are commonly connected, but whose LED and detector sink leads are connected, respectively, to separate sink and detector leads. The arrangement, more specifically described in said copending application, amounts to a novel multiplexing scheme wherein each LED and each detector can be selectively activated or accessed in any order desired, by choosing or addressing one of plural source leads, one of plural sink leads, and one of plural detector leads. For a 4×8 matrix, having 32 combination optical sensor units, 8 source busses, 4 sink busses, and 8 detector busses are required. Two additional lines corresponding to detector busses are required for reading a non-optical sensor, in particular, a Hall effect detector used in the sealer unit to detect mis-sealed envelopes. In a typical addressing cycle, a desired source bus is addressed and turned on, and simultaneously a desired detector bus. This activates only the photodetector, which will then detect ambient light. The resultant detector current would be read and temporarily stored. Immediately thereafter, the desired LED sink line is grounded to produce LED radiation, and a second reading of the detector current made and compared with the recorded ambient value. This sequence would occur during each optical sensor read sub-cycle and would typically consume about 20 uS.

Since the machine could be used in a well-lighted room, or even on occasion exposed to sunlight, it is important that the detector output responding to the LED radiation (reflected or direct), substantially exceeds that produced by bright ambient light, so that the latter can be subtracted from the former, leaving a strong useful signal. To achieve this result, the LED is pulsed hard, meaning driven at a current level about its rating to increase its light output. Such LEDs can tolerate pulsed overloading for a short time interval. If by accident the pulse is not terminated within a certain time, then the LED will overheat and burn-out.

The Watchdog module functions to prevent LED overheating. It does this by being executed during each cycle after all optical sensors have been read, and generating a pulse to a hardware circuit connected to the sensor bus processor if current is detected in any of the LED sink lines. This hardware circuit when pulsed by the Watchdog pulse will prevent resetting of the sensor bus processor for its next cycle. In effect, if at the end of each cycle LED sink current is detected (which should have terminated), the Watchdog pulse ensures that the LED source lines cannot be re-activated during the next cycle. Hence, the LEDs remain off.

The main program block 300 includes an executive routine for sequentially calling and executing the software modules. This software will be responsible for reading and sending the sensors, status to the shared NVM memory buffer. Certain sensors will be required to scan at faster rates than others, but all sensors will be scanned within a 10 ms window. Different types of sensors will be handled differently. In addition, sensors of the same type may be sampled at a different rate. A list and a description of the sensors follows below. The following is required for the instance of the described machine:

Flap position sensors, which are optical sensors, should be sampled every 0.056" approximately of mailpiece advance (about 0.5 ms at peak velocity). A majority function will be applied around the position found in the last reading. The change allowed from one reading to another is up to 2 positions.

Fast optical sensors are sensors which require frequent sampling (on the order of every 2 ms). An analog to digital (A/D) mechanism is used, and there is a need to read the background value for these sensors.

Slow optical sensors, are sensors that require slow sampling rates (approximately 10 msec). An A/D mechanism is also used, and there is a need to read the background value for these sensors also.

Hall effect sensors are sensors which require frequent sampling (on the order of ever 8 ms for mail flow sensors).

Shared NVM Memory Buffer is a common RAM which will be shared by other processors within the system. This RAM must be able to handle a loading from the sensor CPU of approximately 40 microseconds every 500 microseconds. All sensor status and commands will be channeled through this RAM.

This particular machine was designed with an 8051 type controller as the sensor controller, an 80196 type controller as the motor controller, and an 80186 type processor as the host.

The 11 modules of the, software is comprised of: (1) COMM_RAM 301, (2) FLAP_READ 302, (3) POST NIP 303, (4) MAIL_2 304, (5) OPTICAL_SLOW 305, (6) SEAL_EXFLW 306, (7) MAIL_4 307, (8) WATCHDOG 309, (9) HALL_EFFECT 310, (10) INIT_SENSORS 311, and DELAY_1 312. After the initialization of the sensor bus hardware by the routines in the INIT_SENSORS module 311, the executive in the MAIN block 300 will call the COMM_RAM routine, which, upon completion, the following sequence of events will take place.

The FLAP_READ module 302 will be executed. The flap sensors will be read and stored in a buffer. Next, the POST_NIP module 303 will be executed and then the post nip sensor data will be saved. Next, the MAIL_2 module 304 is executed which reads and stores the mail #2 sensor. Next, the OPTICAL_SLOW module is executed, and a slow optical sensor will be read and saved. Next, the SEAL_EXFLW module 306 will be executed. Depending on a 'toggling bit', either the sealer exit or sealer flow sensor will be read and saved. All this collection of data will be done in approximately 546 microseconds.

Next, the executive program will start again by calling the COMM_RAM 301 routine and then again read the flap sensors 302, the post nip 303, but now will jump to and execute the MAIL_4 module 307, which will read the mail #4 sensor, then do a watchdog 309, and then another slow optical sensor will be read. Then, it will execute the HALL_EFFECT module and read the status of the stripper arm sensor. Again, all data collection since COMM_RAM started will be done in approximately 552 micro seconds. The Delay_1 routine 312 is an approximately 14 usec delay used by the FLAP_READ module.

The 8051 from power up will jump to a vector location which will do an initialization of software and hardware and then follow in a sequential type format as summarized below.

Since there are no interrupts in the mail-flow mode, all modules will have the same priority level; however the time critical modules will be executed more often than other modules:

| INIT_SENSORS | | |
|---|---|---|
| COMM_RAM | | 1ST EVENT |
| FLAP_READ | (with DELAY_1) | 2ND EVENT |
| POST_NIP | | 3RD EVENT |
| MAIL_2 | | 4TH EVENT |
| OPTICAL_SLOW | | 5TH EVENT |
| SEALER_EXFLW | | 6TH EVENT |
| COMM_RAM | | 7TH EVENT |
| FLAP_READ | (with DELAY_1) | 8TH EVENT |
| POST_NIP | | 9TH EVENT |
| MAIL_4 | | 10TH EVENT |
| WATCHDOG | | 11TH EVENT |
| OPTICAL_SLOW | | 12TH EVENT |
| HALL_EFFECT | | 13TH EVENT |

The above sequence of events will occur somewhere between 1 ms and 1.5 ms depending on the loading of the program. In the diagnostic mode, the Camera Strobe flag is checked after each event is executed.

Certain sensor flags will be only set in software; the clearing of these flags will be done by the motor controller when it accesses the data. This is to ensure that the motor controller does not miss any active flags which could change states within two 500 microsecond periods. The setting and resetting of these flags is not important to an understanding of the present invention. The module INIT_SENSORS 311 will initialize the sensor bus to its proper states including internal and external registers. The DELAY_1 module 312 is preferably a sub-module of the flap read module 302 and delays approximately 14 micro seconds.

A description of the functions of each of the modules now follows.

POST_NIP, a task which will read an optical sensor in the feeder module which the motor controller will use to see the gap differences between two envelopes. Each module will generally follow the same procedure as below except for those modules which share a time slice and which toggle a bit every time to decide which of the two sensors to process.

A source enable line of the LED-detector matrix will be activated; at this time an A/D address is also selected. Then an A/D start conversion command is given for collecting the background of the sensor. Next, a delay of approximately 10 microseconds follows to allow the A/D to settle. The A/D result of the sensors background is read, added to an offset condition and saved. Next, the A/D conversion of the sensor for its state condition is started. Again, a delay of approximately 10 microseconds, and the A/D result of the sensor is read. The sensor's state with its background is compared and a bit in a buffer set accordingly. It will be appreciated that the LED-photodetector units described generate analog data. In all cases, the analog data is converted with known hardware or software to digital data, and the digital data stored in the shared RAM. The motor controller is programmed to respond to the digital data it reads from the shared RAM.

The FLAP_READ module is executed after every COMM_RAM task is completed, which is approximately 500 microseconds. A timer overflow which corresponds to a fixed distance traveled by the envelope will set a bit in the flap data buffer. The module will also read the sensor data and determines what part of the array is covered by the flap, which will tell us where the flap edge is every approximately 500 micro seconds.

The steps to be taken to read the detectors around the last recorded edge of the flap are:

1. Turn on sink and source according to a pointer;
2. Wait for 10 us;
3. Read detectors;
4. Filter the 2 relevant detectors and determine their state;
5. Increment a counter by the number of covered detectors;
6. Repeat 1-5 for 4 source and sink combinations;
7. If counter >6 increment array count by 2 else if counter >4 increment array count by 1 else if counter=4 do nothing else if counter <4 decrement array count by 1 else if counter <2 decrement array count by 2
8. Place the flap data in the buffer for the COMM_RAM routine.

A more complete description of this sequence of steps can be found in the referenced copending patent application, Ser. No. 291,092.

The array count (flap position) will be saved in the buffer and updated to the NVM RAM every time the module COMM_RAM is executed.

MAIL_2, a task which will read an optical sensor on the integrated module which will tell the motor controller processor when to start slowing down.

SEAL_EXFLW, a task which will read the sealer exit sensor within 500 microseconds and then within the next 500 microseconds switch a bit ("toggling bit") and read the sealer flow sensor and prepare both states for the shared NVM-RAM.

MAIL_4, a task which will read the mail #4 sensor approximately every 1.5 milliseconds and prepare its status for the shared NVM-RAM.

HALL_EFFECT, this routine will read the stripper arm Hall-effect sensor every 1 millisecond, and prepare its status for COMM_RAM.

WATCHDOG, a task which will give a pulse to a hardware circuit every 1 millisecond to keep the hardware circuit from resetting the sensor bus processor. The pulse will be available at a port pin of the sensor controller.

COMM_RAM, is a driven task, communicating with the shared NVM-RAM for transfer of data in both directions to the sensor processor. The motor controller will read and write to some of the same NVM-RAM locations, hence, providing a communication link. The COMM_RAM is the first module called by the executive. This module is executed every approximately 500 micro seconds.

This task will first go out and read a mode command from the NVM-RAM buffer, which was updated by the motor controller. The mode command will indicate mailflow mode, tape mode, or diagnostic mode. The mailflow mode will be when the system is just handling envelopes (seal or non seal mode), the tape mode is for just producing tapes, and the diagnostic mode is to test the machine's performance or correct malfunctions. This read function will be performed by first doing a dummy read to the NVM and then waiting for the data available signal to be enabled, at this time another read will be done which will include the command from the motor controller. Depending on the command, one of the three described above, a buffer or buffers will be updated to the NVM-RAM in the following manner; the first buffer of status will be send to the NVM-RAM with no wait conditions; the next write of status will wait for the data available signal to be enabled and at this time will send its status; this format will follow for all writes to the NVM-RAM except for the first write cycle. A typical process is as follows.

Read to memory mapped NVM ram location; wait for data available enable; read memory-mapped NVM-RAM location again and keep data; if data is equal to mail mode, then give mail mode data, else if data is equal to tape mode then give tape mode data, else if data is equal to diagnostic mode give diagnostic data.

The task of the OPTICAL_SLOW module is executed every approximately 500 microseconds (after every COMM_RAM task) and its purpose is to scan a different slow optical sensor each time and set a bit representing the state of that sensor in a buffer. This routine can scan all the slow optical sensors listed below within 10 milliseconds.

| Sensor Name | Sensor Type | Module |
|---|---|---|
| mail in hopper | optical | feeder |
| mail width | optical | feeder |
| nozzle clear sealer | optical | sealer |
| water level 1 | optical | sealer |
| water level 2 | optical | sealer |
| water level 3 | optical | sealer |
| water level 4 | optical | sealer |
| water level 5 | optical | sealer |
| mail flow detector 1 | optical | integrated |
| long flap 1 | optical | feeder |
| long flap 2 | optical | feeder |
| shutter open | optical | integrated |
| meter security | optical | integrated |
| key switch | mech switch | integrated |
| temperature #1 | therm | integrated |
| temperature #2 | therm | integrated |

-continued

| Sensor Name | Sensor Type | Module |
|---|---|---|
| temperature #3 | therm | integrated |

A typical process is as follows:

Using a table with an offset, the source enable line of address is set up and an A/D start conversion command is given to determine background radiation; a delay of approximately 10 microseconds follows after which the A/D result of the sensor background is read and stored. Next, using a table with an offset, the sink enable line is activated, an A/D conversion is started for the sensor state condition, again a delay of approximately 10 microseconds, and the A/D result of the sensor is read and stored. Next, the sensor's state with its background is compared and a bit in a buffer set accordingly.

In the diagnostic mode, a camera strobe flag will be checked after each module routine is executed. If the flag is set, then a strobe took place during the time the module was checking sensors and therefore the same module will be executed again; if the flag is not set then the program will execute the next sequential module.

An internal ROM will hold the program. A data structure first BUFFER will hold the sensor's data as it is read from the ports and the post nip status. A data structure second BUFFER will hold the arranged sensor data for the NVM-RAM. It will use part of the bit addressable locations in the RAM. The times that follow are for how often COMM_RAM sends this data to the NVM. For the first BUFFER, every approximately 550 usec; for the second BUFFER, every approximately 1 ms. This does not mean that the sensors are sampled at these times; the sampling rate is given below in Table 2.

Figure 6:
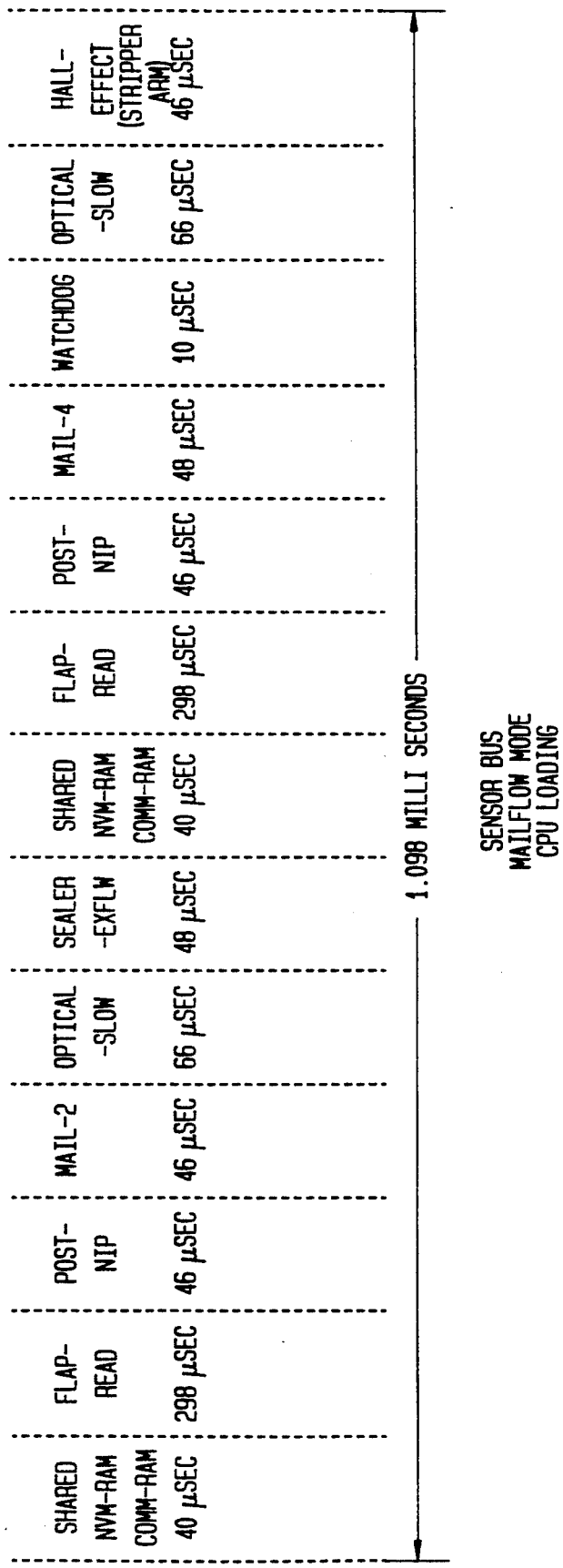
FIG. 6 illustrates the sensor processor main processing cycle divided up into time slices for execution of the modules illustrated in FIG. 5.

This also indicates the loading of the sensor controller (CPU), and will be best understood with reference to a timing chart depicted in FIG. 6.

The timing chart of FIG. 6 shows a typical main sensor cycle which in this example occupies about 1.1 ms, divided into 13 times slices with their duration listed. During each time slide, the indicated module is executed. The scan rates for each module are listed in table 2 below. The times given are approximate values.

TABLE 2

| MODULE | SCAN RATES |
|---|---|
| SHARED NVM (COMM_RAM) | 549 usec |
| FLAP_READ | 549 usec |
| POST_NIP | 549 usec |
| MAIL_2 | 1.098 ms |
| OPTICAL_SLOW | 549 usec |
| SEALER_EXFLW | 2.196 ms |
| MAIL_4 | 1.098 ms |
| WATCHDOG | 1.098 ms |
| HALL_EFFECT | 1.098 ms |

A functional description of the sensor follows below:

| # | Name | Location | Type | Quantity | Sample Rate |
|---|---|---|---|---|---|
| 1 | Mail in hopper | FD | OR | 3 | 10 ms |
| 2 | Mail thickness | FD | HE | 6 | <20 ms |
| 3 | Post nip | FD | OR | 1 | 500 us |
| 4 | Mail Width | FD | OR | 1 | 10 ms |
| 5 | Long Flap | FD | OR | 2 | 10 ms |

-continued

| # | Name | Location | Type | Quantity | Sample |
|---|------|----------|------|----------|--------|
| 6 | Flap Detector | SL | OR | 23 | 500 us |
| 7 | Sealer exit | SL | OR | 1 | 2 ms |
| 8 | Stripper arm | SL | HE | 1 | 1 ms |
| 9 | Nozzle clr SL | SL | OR | 1 | 10 ms |
| 10 | Water Level | SL | OR | 5 | 10 ms |
| 11 | Sealer Mail Flow | SL | OR | 1 | 2 ms |
| 12 | Mail flow #1 | IM | OR | 1 | 10 ms |
| 13 | Mail flow #2 (OSA) | IM | OR | 1 | 1 ms |
| 14 | Mail flow #4 (OSB) | IM | OR | 1 | 2 ms |
| 15 | Shutter Open/Back | IM | OR | 1 | 10 ms |
| 16 | Shutter Home/Wait | IM | OR | 1 | 10 ms |
| 17 | Shutter Init. | IM | OR | 1 | 10 ms |
| 18 | Meter Security | IM | OR | 1 | 10 ms |
| 19 | Key Switch | IM | SW | 1 | 10 ms |
| 20 | Temperature | IM | THER | 3 | 10 ms |
| 21 | Tape Unit Water | TP | OR | 1 | 10 ms |
| 22 | Out Of Tape #1 | TP | HE | 1 | 10 ms |
| 23 | Out Of Tape #2 | TP | HE | 1 | 10 ms |
| 24 | Tape Exit Moist | TP | OR | 1 | 1 ms |
| 25 | Tape Exit Knife | TP | OR | 1 | 1 ms |
| 26 | Carriage Feed | TP | HE | 1 | 1 ms |
| 27 | Knife Home | TP | HE | 1 | 1 ms |
| 28 | Tape Exit Home | TP | HE | 1 | 1 ms |

FD = feeder. SL = sealer. IM = integrated module. TP = tape. OR = optical reflector, HE = Hall effect, SW = switch.

Sensor #1: Mail in Hopper—Sensor is used to determine when mail is in the mail hopper.

Sensor #2: Mail Thickness—Sensor is used to determine mail thickness.

Sensor #3: Post Nip—Sensor is used to register mail at the feeder exit to the sealer.

Sensor #4: Mail Width Sensor—Sensor is used to tell if a wide envelope is to be fed through the machine.

Sensor #5: Long Flap Sensor—Sensors are used to determine when envelope flaps are too long to process without reducing system speed.

Sensor #6: Flap Profile Sensor—Sensor is used to detect the envelope flap edge position along the entire length of the envelope as it passes the sensor. The resulting flap length profile is used for positioning of the nozzle to spray water on the envelope flap.

Sensor #7: Sealer Exit—Sensor is used to detect the envelope leaving the sealer to prevent feeding the next letter if there is a jam in the sealer.

Sensor #8: Stripper Arm Motion Detector—Sensor is used to detect the motion of the stripper arm if it moves which it should do only if the stripper has jammed in an envelope flap.

Sensor #9: Nozzle Clear Sealer Assy.—Sensor is used to determine if the spray nozzle is clear or to prime the pumping system.

Sensor #10: Water Level—Sensor is used to determine the level of water in the bottle at five discrete positions. The positions are full, ¼, ½, ¾ and empty.

Sensor #11: Sealer Mail Flow—Sensor is used to determine the position of the mail at various times in the mail path through the transport.

Sensor #12: Mail flow detector #1.—Sensor is used to determine when an envelope is entering the integrated module.

Sensor #13: Mail flow detector #2.—This sensor works with the #14 sensor to decelerate the envelope, so proper registration can take place.

Sensor #15: Shutter Open/Back—Sensor is used to verify if the meter shutter is in the open or back position.

Sensor #16: Shutter Home/Wait—Sensor is used to verify if the meter shutter is in the home or wait position.

Sensor #17: Shutter Init—Sensor is used for initialization of the shutter bar drive.

Sensor #18: Meter Security—Sensor is used to verify that the meter is installed in the machine.

Sensor #19: Key Switch—Detect Meter position:
1—Meter may be removed.
2—Meter disabled.
3—Meter can be used.

Sensor #20: Temperature—Controls the fan according to the temperature.

Sensor #21: Tape Unit Water Level—Sensor is used to sense when the water level within the tape moistener tank is sufficient or insufficient. If it senses insufficient the sealer is told to pump water to it and when it senses sufficient, the sealer is told to stop pumping.

Sensor #22: Out of Tape #1—Sensor is used to determine when the tape units roll 1 has run out of tape. This sensor is mechanically coupled to the tape de-reeler.

Sensor #23: Out of Tape #2—Sensor is used to determine when the tape units roll 2 has run out of tape. This sensor is mechanically coupled to the tape de-reeler.

Sensor #24: Tape Exit Moistener—Sensor is used to determine when the tape is at the end of the moistener conveyer to stop the conveyer and to inhibit the next tape until the present tape is removed.

Sensor #25: Tape Exit Knife—Sensor is used to verify a number of functions such as tape did not jam at knife and that the tape was cut by knife and also used in the tape initialization process.

Sensor #26: Carriage Feed Pos.—Sensor to position the tape carriage at its feed position.

Sensor #27: Knife Home—Sensor is used to determine when the knife assembly is in its home position.

Sensor #28: Tape Exit Home—Sensor is used to verify if the tape exit mechanism is in the home or open position.

The Flap detector is described in detail in the referenced copending application, Ser. No. 291,092, and need not be further described here.

Some sample code, in assembly language, is given below. It will illustrate generally how the COMM_RAM and OPTICAL_SLOW modules operate.

| COMM RAM: | | |
|---|---|---|
| PUSH | ACC | |
| CLR | P2.4 | ;enable sense lines address |
| MOV | A,PO | ;read sense lines, addr. = 0 |
| ANL | A,#OFH | ;mask |
| SETB | P2.4 | ;disable u2 side |
| COMM RAM: | | |
| MOV | R2,A | ;save |
| JNZ | Another_Mode | ;if not zero check; |
| MOV | PO, FAST_BUFF | ;196 latch has fast buffer data |
| CLR | P3.7 | ;enable 196 latch |
| SETB | P3.7 | ;data to latch |
| JNB | P3.5, SELF | ;wait for handshake |
| MOV | PO,MED_BUFF | ;medium buffer to data bus |
| CLR | P3.7 | ;latch medium buffer to 196 latch |
| SETB | P3.7 | ;data to latch |
| JNB | P3.5,SELF1 | ;wait for 196 handshake |
| MOV | RO,SLOW_POINTER | ;next slow data to send onward to 196 |
| MOV | PO,@R | ;slow pointer data to the data bus |
| CLR | P3.7 | ;196 latch enable |
| SETB | P3.7 | ;data bus to latch |

-continued

| | | |
|---|---|---|
| INC | R0 | ;get slow pointer ready for next time |
| CJNE | R0, #25H, ONWARD | ;check if slow pointer needs reset |
| MOV | SLOW_POINTER, #22H | ;if reset needed set to 22H |
| COMM RAM: | | |
| ONWARD: | | |
| POP | ACC | |
| RETI | | |
| ANOTHER_MODE: | CHECK FOR # AND ACT ACCORDINGLY. | |

Total time for COMM_RAM with the fast first buffer and the medium second buffer data sent every 500 microseconds and three slow buffers within approximately 1.5 ms=about 35 microseconds.

| | | |
|---|---|---|
| OPTICAL SLOW: | | |
| MOV | DPTR,#SLOW_TABLE_SOURCE | ;beginning of slow entries |
| MOV | A,INDEX | ;offset for all tables |
| MOV | R6,A | ;temp buffer |
| MOVC | A,@A + DPTR | ;next source enable to acc |
| MOV | P1,A | ;source enable to outside world |
| MOV | DPTR,#AD_ADDRESS | ;beginning of ad address entries |
| MOV | A,R6 | ;offset for ad address |
| OPTICAL SLOW: | | |
| MOVC | A,@A + DPTR | ;next ad ready |
| MOV | P0,A | ;ad address to outside world |
| SETB | P3.6 | ;give ad start pulse |
| CLR | P3.6 | |
| NOP | X7 | ;approximately 10 micro sec delay |
| SETB | P2.6 | ;ready to read ad background |
| MOV | A,P0 | ;ad result to acc |
| ADD | A,#OFFSET | ;adjust with offset |
| MOV | R5,A | ;save adjusted value |
| CLR | P2.6 | ;disable read |
| SETB | P3.6 | ;start another ad convert |
| CLR | P3.6 | |
| MOV | DPTR,#SLOW_SINK_TABLE | ;all sink entries begin here |
| MOV | A,R6 | ;offset to acc |
| MOVC | A, @A + DPTR | ;next sink to acc |
| MOV | P2,A | ;sink enable to outside world |
| OPTICAL SLOW: | | |
| NOP | X7 | ;delay approximately 10 micro sec |
| CLR | C | |

-continued

| | | |
|---|---|---|
| SETB | P2.6 | ;enable ad for read |
| MOV | A,P0 | ;sensor state to acc |
| CLR | P2.6 | ;disable ad read |
| SUBB | A,R5 | ;check for 0 or 1 |
| JC | ITS_ZERO | ;backgnd greater sens = 0 |
| SETB | C | ;sensor active = 1 |
| MOV | INDEX, C | ;set proper sensor with state |
| INC | INDEX | ;set next slow optical offset |
| CJNE | INDEX,#25D, SKIP | ;last buffer location |
| MOV | INDEX,#0 | |
| SKIP: | | |

Total time about 66 micro-seconds.

It will be understood from the foregoing that the sample code given is for a particular machine and is represented of a typical program that could be used. The invention, of course, is not limited to the use of that code. Nor is it limited to the module execution sequence or the cycle times given or the division of the cycle into the time slices as shown. Modifications of the foregoing will be evident to those skilled in the art for different mail-handling machines using different sensors located differently and performing the functions required to enable the machine to process mail at a high speed.

While the invention has been described and illustrated in connection with preferred embodiments, many variations and modifications as will be evident to those skilled in this art may be made therein without departing from the spirit of the invention, and the invention as set forth in the appended claims is thus not to be limited to the precise details of construction set forth above as such variations and modifications are intended to be included within the scope of the appended claims.

What is claimed is:

1. In a high speed mail-handling machine capable of processing mixed mail of varying thickness and size, said processing including at least the steps of transporting each mailpiece to a weighing station and weighing each mailpiece and then printing indicia on the weighed mailpiece, said processing being activated and controlled by a drive controller in accordance with a plurality of sensors distributed throughout the machine, the improvement comprising providing a sensor processor dedicated to the task of accessing the sensors to determine their state and communicate the sensor's states to the drive controller, and causing the sensor processor to access the sensors and communicate their state to the drive controller wherein the sensor processor being caused to activate the sensors before collecting their status, and wherein some of the sensors are optical sensors, and the activation step includes measuring the background radiation before collecting their status.

2. The mail-handling machine processing as claimed in claim 1, wherein the communication step is carried out by writing the sensor data to a RAM which the drive controller can also access.

* * * * *